United States Patent [19]

Todd, Jr.

[11] Patent Number: 5,053,240

[45] Date of Patent: Oct. 1, 1991

[54] NORBIXIN ADDUCTS WITH WATER-SOLUBLE OR WATER-DISPERSIBLE PROTEINS OR BRANCHED-CHAIN OR CYCLIC POLYSACCHARIDES

[75] Inventor: Paul H. Todd, Jr., Kalamazoo, Mich.

[73] Assignee: Kalamazoo Holdings, Inc., Kalamazoo, Mich.

[21] Appl. No.: 426,578

[22] Filed: Oct. 24, 1989

[51] Int. Cl.$^5$ .................................................. A23L 1/27
[52] U.S. Cl. .................................................. 426/540
[58] Field of Search .............. 426/540; 530/354, 360, 530/365; 536/2, 3, 56, 102, 103, 114

[56] References Cited

U.S. PATENT DOCUMENTS

| | | | |
|---|---|---|---|
| 2,831,775 | 4/1958 | Kocher | 426/540 |
| 3,110,598 | 11/1963 | Muller et al. | |
| 3,455,838 | 7/1969 | Marotta et al. | |
| 3,790,688 | 2/1974 | Walter et al. | 426/540 |
| 3,943,262 | 3/1976 | Winkler et al. | |
| 4,061,786 | 12/1977 | Winkler et al. | |
| 4,167,587 | 9/1979 | Danforth | 426/540 |
| 4,187,323 | 2/1980 | Gidlow | 426/540 |
| 4,380,553 | 4/1983 | Schmidt | |
| 4,475,919 | 10/1984 | Woznicki et al. | |
| 4,548,822 | 10/1985 | Schmidt | |
| 4,699,664 | 10/1987 | Hettiarachchy et al. | 106/459 |

FOREIGN PATENT DOCUMENTS 0200043 9/1986 European Pat. Off. .

OTHER PUBLICATIONS

Szejtli, J. 1981, "Cyclodextrins in Foods, Cosmetics and Toiletries", Proceedings of the First International Symposium on Cyclodextrins, Reidel Publishing Company, Dordrecht, Holland.
Govindarajan, S. and Morris H. A., 1973, "Pink Discoloration in Cheddar Cheese", Journal of Food Science, vol. 38, p. 675.

Primary Examiner—Donald E. Czaja
Assistant Examiner—John Mowbray
Attorney, Agent, or Firm—Gordon W. Hueschen

[57] ABSTRACT

A norbixin complex with a water-soluble or water-dispersible branched-chain or cyclic polysaccharide or a water-soluble or water-dispersible protein, which will not precipitate upon standing in water, which gives an essentially stable bright reddish or magenta solution in water, and from which complex norbixin cannot be removed by centrifugation, as well as a process for preparing such a complex of norbixin and a substrate, selected from a water-soluble or water-dispersible branched-chain or cyclic polysaccharide and a water-soluble or water-dispersible protein, by contacting the substrate and norbixin in an aqueous solution at an alkaline pH, e.g., above about 8.5, at which pH the norbixin is present in its water-soluble orange alkaline form, and then acidifying to drop the pH to below about 7.7, preferably below about 6.8, thereby complexing the norbixin in its neutral to acidic reddish or magenta form with the substrate, are disclosed.

41 Claims, 5 Drawing Sheets

NORBIXIN ADDUCTS WITH WATER-SOLUBLE OR WATER-DISPERSIBLE PROTEINS OR BRANCHED-CHAIN OR CYCLIC POLYSACCHARIDES

BACKGROUND OF THE INVENTION AND PRIOR ART

1. Field of Invention

Clear reddish water-soluble norbixin adducts with improved tinctorial power and stability in light and under acidic conditions.

2. Background of the Invention

This specification describes a new and novel adduct form of norbixin, a dicarboxylic acid carotenoid derived from annatto seed.

This seed is produced by a tropical bush, indigenous to the Amazon basin and presently cultivated in the tropics throughout the world. The outside of the seed is covered with as much as 1% to 2% bixin, which is the monomethyl ester of norbixin. The bixin is readily removed from the fresh seeds as a paste, and as such is used as a cosmetic and food color by the peoples indigenous to the Amazon area. Since settlement of the New World, it has become a common colorant for fats, in its paste form, and more recently has been refined and prepared as a microcrystalline suspension in vegetable oil or as a more dilute solution in vegetable oil. These forms of bixin are used to color margarine, butter, frying oils and, when dispersed on carriers such as salt, as seasonings for sauces and the like. Preparations comprising bixin are now generally made by solvent extraction and purification of the pigment.

Norbixin, being saponified bixin, is made by the alkaline saponification of bixin. This is most commonly done by extracting the seeds with aqueous alkali and heating. The resulting product, known commercially as "cheese color", is the basis of the coloring of most cheddar cheeses. It is added directly to the churn or milk, which is acid, and which precipitates the norbixin, which in turn colors the butterfat during fermentation. This direct alkaline extract contains other alkali-soluble materials, many of which are brownish in shade, and these also contribute to the coloration of the cheese. This tends to reduce the chroma, which is the equivalent of introducing more gray into the pigment. For applications which require a higher chroma, norbixin is made by saponification of relatively pure bixin, which has been prepared by crystallization from a solvent such as ethyl acetate or chloroform. This improves the chroma, and therefore the brightness of the color. Such type of product may be used to give an orange cast to cereals, by addition of the alkaline norbixinate solution or powder to the dough, wherein norbixin precipitates due to the acidity. Upon cooking, it distributes the orange color throughout the batter.

Because norbixin made from pure bixin—75% pure or more—has greater chroma and purity of hue, it is the preferred form of norbixin for use in forming the adduct described in this specification. However, the less pure, conventional cheese color types may also be employed where purity of color is not of paramount significance.

Norbixin is insoluble in water, whereas the salts, such as potassium norbixinate (very soluble) and sodium norbixinate (less soluble), dissolve under alkaline conditions to give an orange color. These salts are available in dry as well as liquid form, either admixed with an alkaline earth carbonate carrier, or dried and mixed with a modified food starch. These dry products have the same properties as the aqueous norbixinate solutions, being dispersible in water, possessing an orange shade, and being useful for mixing into flours or seasoning. In addition, norbixin may be precipitated from its norbixinate solution by the addition of acid, and the resulting liquid dispersed on salt to give a product suggested for seasoning salt coloration.

The art also shows the preparation of a "lake" type water-insoluble coloring made by admixing norbixinate solution with cellulose, boiling, adding salt to "fix" the pigment on the cellulose, removing the water and excess norbixinate by filtration, and washing finally with very dilute acetic acid to provide a neutral powder. The color, while brownish, and not the orange of the conventional norbixinate preparations, is said to be suitable for coloring tablets. It is not suggested for use as a food coloring.

Additionally, norbixinate preparations are made using polysorbate 80 and optionally propylene glycol. The polysorbate 80 is a common food grade emulsifier and, upon addition to acidic media the norbixinate in solution in the polysorbate 80 changes to norbixin, which remains emulsified by the polysorbate 80. These solutions are orange, and their chroma and purity will depend upon the purity of the bixin used to make the norbixinate. They are called "acid-stable" annatto colors, and are useful in sauces and dressings.

An understanding of the adduct described in this specification is assisted by using the empirical formulas and molecular weights of the annatto carotenoids:

| | | | |
|---|---|---|---|
| bixin: monomethyl ester, mono free carboxylic acid | | | |
| | $C_{25}H_{40}O_4$ | MW | 394 |
| norbixin: dicarboxylic acid | | | |
| | $C_{24}H_{38}O_4$ | MW | 380 |
| norbixinate alkaline salt of norbixin: | | | |
| potassium | $C_{24}H_{36}O_4K_2$ | MW | 456 |
| sodium | $C_{24}H_{36}O_4Na_2$ | MW | 424 |

As described above, the norbixinates become free norbixin upon addition to foodstuffs, which are acidic, and wherein they express their expected orange to orange-brown color.

BRIEF DESCRIPTION OF THE DRAWINGS

The invention will be better understood by reference to the drawings, wherein all FIGS depict absorption spectra of various complexes or adducts of the invention and of corresponding uncomplexed or unadducted materials for comparison, and wherein.

OBJECTS OF THE INVENTION

Figure 1:
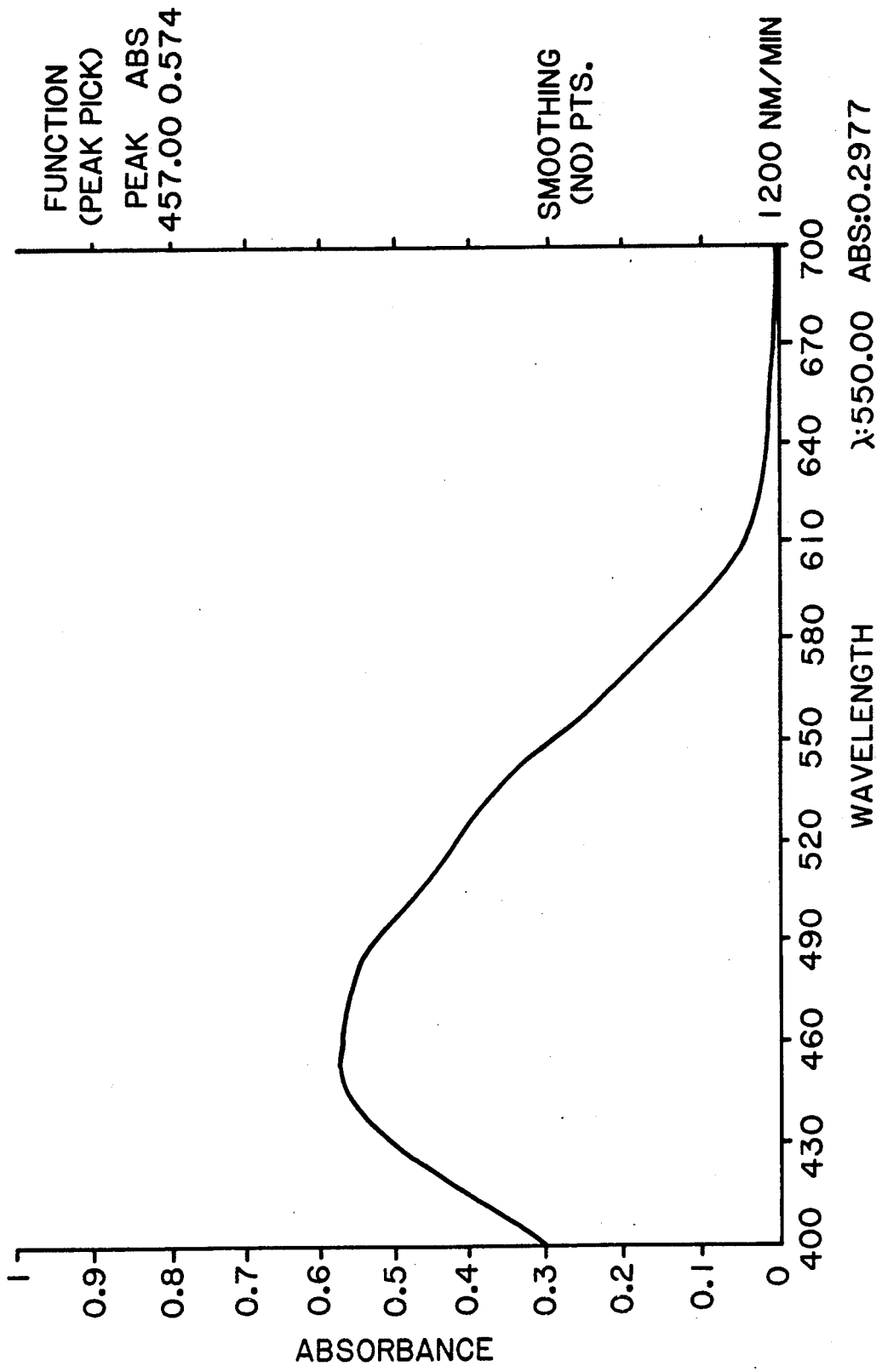
FIG. 1 is an absorption spectrum of a norbixin-gum arabic adduct of the invention diluted in water at pH3 and showing no peaks but showing considerable absorbance at 550 nm.

It is an object of the present invention to provide novel and stable complexes or adducts of norbixin with substrates selected from polysaccharides and proteins and a method for the production thereof. It is a further object of the invention to provide such a complex or adduct which is produced by acidification from an alkaline solution of norbixin and a substrate, which will not precipitate upon standing in water, which gives an essentially stable reddish to magenta (and not the usual alkaline orange) solution in water at pH3–4, and from which adduct or complex norbixin cannot be removed by centrifugation at neutral to acidic pHs. A still further object is to provide such novel adducts or complexes in which norbixin is complexed to a plurality of substrates and coacervates of such complexes. Another object is the provision of such an improved norbixin product and a process for production thereof, with all of the attendant advantages of the stable norbixin complex or adduct upon its use in the coloring of foods, drinks, and the like. Additional objects will become apparent hereinafter as the description proceeds, and still others will be obvious to one skilled in the art to which this invention pertains.

SUMMARY OF THE DISCLOSURE

The invention, then, inter alia, comprises the following, alone or in combination:

A process for preparing a complex of norbixin and a substrate selected from a water-soluble or water-dispersible branched-chain or cyclic polysaccharide and a water-soluble or water-dispersible protein which comprises admixing the substrate and norbixin in an aqueous solution at a pH above about 8.5, at which pH the norbixin is present in its water-soluble orange alkaline form, and then acidifying to drop the pH to below about 7.7, thereby complexing the norbixin in the reddish or magenta form of its complex with the substrate; such a process wherein the substrate is selected from milk protein, sodium caseinate, whey, gelatin, modified food starch, pectin, a vegetable gum, propylene glycol alginate, cyclodextrin, maltodextrin derived from amylopectin, and carboxymethylcellulose; such a process wherein the pH of the aqueous solution prior to acidification is above about 9 and the pH after acidification is below about 6.8; such a process wherein the pH of the aqueous solution is about 9–12 and the pH after acidification is about 6–6.7; such a process wherein the norbixin complex is formed into a coacervate; such a process wherein the norbixin is complexed with a combination of substrates; such a process wherein the combination of norbixin complexes is formed into a coacervate; such a process wherein the substrate is a combination of gelatin and a vegetable gum; such a process wherein the combination of gelatin-gum norbixin complexes is formed into a coacervate; such a process wherein the substrate is a combination of gelatin and gum arabic; such a process wherein the combination of gelatin-arabic norbixin complexes is formed into a coacervate; such a process wherein the substrate is gelatin, gum arabic, gum karaya, gum ghatti, modified food starch, cyclodextrin, or carboxymethylcellulose; such a process wherein the substrate is cyclodextrin; such a process wherein the process is carried out in the presence of a water-miscible, non-acidic solvent which does not interfere with the complexing of the alkaline norbixin with the substrate; such a process wherein the solvent is selected from the group consisting of alcohols, glycerine, and propylene glycol; and such a process wherein the solvent is ethyl alcohol, isopropyl alcohol, glycerine, or propylene glycol.

Moreover, a norbixin complex with a water-soluble or water-dispersible branched-chain or cyclic polysaccharide or a water-soluble or water-dispersible protein, which will not precipitate upon standing in water which gives an essentially stable reddish or magenta solution in water at a pH of 3 to 4, which has an increased absorption at 550 nm and a reduced absorption in the 460–550 nm range when compared with norbixin or norbixinate, and from which complex norbixin cannot be removed by centrifugation at a neutral to acidic pH; such a complex wherein the substrate is selected from milk protein, sodium caseinate, whey, gelatin, modified food starch, pectin, a vegetable gum, propylene glycol alginate, cyclodextrin, maltodextrin derived from amylopectin, and carboxymethylcellulose; such a complex of norbixin with a substrate selected from a water-soluble or water-dispersible branched-chain or cyclic polysaccharide and a water-soluble or water-dispersible protein, the norbixin being complexed to the substrate by acidification from an alkaline solution of norbixin and substrate; such a norbixin complexed with a water-soluble or water-dispersible branched-chain or cyclic polysaccharide or a water-soluble or water-dispersible protein by a process which comprises contacting the substrate and norbixin in an aqueous solution at a pH above about 8.5, at which pH the norbixin is present in its water-soluble orange alkaline form, and then acidifying to drop the pH to below about 7.7, thereby complexing the norbixin in the reddish form of its complex with the substrate; and such a norbixin complexed with a water-soluble or water-dispersible branched-chain or cyclic polysaccharide or a water-soluble or water-dispersible protein according to any of the procedures mentioned in the foregoing.

Moreover, the process of mixing norbixin and liquid whey or skim milk, agitating the mixture at an alkaline pH above about 8.5, dropping the pH to below about 7.7, and then drying; and a dry milk solid product produced by such method, Further, a food or beverage colored with an adduct of norbixin with a water-soluble or water-dispersible protein or branched-chain or cyclic polysaccharide, such a food product wherein the adduct is in dried and powdered form; such a food product wherein the adduct is in liquid form.

Finally, a process as mentioned in the foregoing wherein the pH above about pH 8.5 is effected with NaOH or KOH; and such a process wherein the downward pH adjustment is effected using phosphoric acid.

THE INVENTION

It has now been found that reddish, acid-stable, liquid or powdered adduct or complexed forms of norbixin, made by the process described hereafter, may be used to impart a bright reddish or magenta color to a food or beverage, as opposed to the orange shades obtainable with the usual norbixinate solutions or powders. The substrate, with which the norbixinate forms the norbixin adduct, may be a water-soluble or water-dispersible branched-chain or cyclic polysaccharide or protein. It differs in chemical constitution from the modified food starch powders made with norbixinate in that it contains only norbixin, and no norbixinate. The adduct has the same water solubility as the substrate, is typically reddish in hue, has a spectrum different from that of norbixin emulsions and from that of norbixinates, and has greater tinctorial power. It offers the food technologist a new kind of annatto color, being different in shade than colors of the prior art. It provides a beverage color made without prooxidant emulsifiers, such as polysorbate 80, and it offers acid stability on a wide range of substrates.

An additional form of this invention consists of a coacervate "double" adduct, preferably made by mixing substrates of opposite ionic change, to form a further new class of colors useful in the preparation of foods.

The term "adduct", when used herein, is used in its conventional sense, to mean a complex molecule formed by association of different molecules into an inclusion complex, in which one compound is contained within the lattice or helix of another compound, or in which two different compounds are tightly bound to one another by hydrogen bonding or the like.

The conditions critical to this invention are readily achieved:

1. The substrate must be a water-dispersible or water-soluble branched-chain or cyclic polysaccharide, or à water-dispersible or water-soluble protein. Straight-chain water-insoluble polysaccharides, such as cellulose, will not work. Examples of operative substrates include milk protein, sodium caseinate, whey, gelatin, modified food starch, pectin, a vegetable gum such as gum arabic, gum karaya, or gum ghatti, propylene glycol alginate, cyclodextrin, maltodextrin derived from amylopectin, and carboxymethyl cellulose.

2. The norbixinate solution must be mixed with the substrate at an alkaline pH, so that adduct formation initiates under alkaline conditions. The pH is therefore at least about 8.5 but preferably at least about 9 and advantageously 10-12. The temperature is preferably ambient, is sometimes advantageously higher, but may sometimes even be somewhat lower.

3. The alkaline solution must be acidified relatively slowly, to enable the norbixinate to form a stable adduct rather than be precipitated as free norbixin. The final pH must be below about 7.7, and is preferably below about 6.8 and optimally about 6 to about 6.7, but may be even lower, such as pH3, if the substrate is not degraded at such lower pH.

Although it is not essential, the preferred form of norbixinate is derived from relatively pure bixin, which improves chroma, purity of color, and solubility of adduct.

The process of the invention may conveniently but not necessarily be carried out in the presence of a water-miscible non-acidic solvent which does not interfere with the adducting or complexing of the norbixin with the substrate and, for example, the solvent may conveniently be selected from the group consisting of alcohols, glycerine, and propylene glycol, most preferably ethyl or isopropyl alcohol, glycerine, or propylene glycol.

The following Examples are given to illustrate the importance of these critical conditions, as well as typical substrates, and applications of the adduct product as compared with prior art norbixinate products, but are not to be construed as limiting.

EXAMPLE 1

Preferred forms of the process and product

Two preferred proteins are skim milk and gelatin, and two preferred branched-chain polysaccharides are gum arabic and carboxymethylcellulose. The basic procedure for forming the adducts is the same: raising the pH of an aqueous solution to at least 8.5, as by the addition of KOH or NaOH, and then adding an alkaline solution of norbixinate, agitating, and slowly acidifying, as with dilute phosphoric acid. The acidified solutions may be used as such, or preferably spray dried to provide a bacteriologically-stable powder.

a. Skim Milk. 200 ml of skim milk was warmed to about 30° C. and the pH was raised from 6.5 to 10.0 with dilute KOH. Then 21 ml of 6.6% potassium norbixinate solution was added, which raised the pH to 10.8. The mixture was agitated for 10 minutes, and then acidified to a pH of 6.5 with 5% phosphoric acid over a period of 12 minutes. The resulting solution of norbixin adduct with skim milk proteins was spray dried. Upon reconstitution to 10% in water, it had the appearance and properties of the pH 6.5 norbixin-skim milk solution, being bright red to magenta in color. Use of liquid whey instead of skim milk gives an equally interesting and highly-colored norbixin adduct product.

b. Gelatin. A 2% solution of 200 bloom gelatin was prepared by warming 4 g of gelatin in 200 ml water to 40° C., at which temperature it was dissolved. The pH was raised to 11 and 2 ml of 6.6% potassium norbixinate solution was added and the mixture agitated for ten minutes. It was acidified over 15 minutes to a pH of 6.8 with 1% H3PO4. It was used as such, or dried and ground to a powder, to impart a bright red color upon dilution in water or juice.

c. Gum Arabic. 30 g of gum arabic were dissolved in 100 ml water and hydrated overnight. It was cooled to 30° C. and the pH raised to 10, whereafter 33 ml of 6.6% potassium norbixinate solution was added and agitated for 20 minutes. The pH was reduced over a fifteen minute period to 6.4, using 5% phosphoric acid. A portion of the solution was spray dried, a portion used as such, and a portion diluted with two parts of propylene glycol and used as such. When added to soda water, all products gave a bright raspberry color. When mixed into a tomato sauce, the brightness and redness was enhanced.

d. Carboxymethylcellulose. A 2% solution of carboxymethylcellulose was prepared by dusting it into 40° C. water and hydrating it for six hours. It was a viscous syrup. The pH was raised to 11, 2% by volume of a 6.6% solution of potassium norbixinate was added, and the mixture agitated for thirty minutes. It was acidified to a pH of 6.5 with 1% H3PO4 over ten minutes, during which time the norbixin-CMC adduct formed. The product was reddish orange and, upon dilution of one part with five parts of water, it was viscous on cooling. In this form it added color and viscosity to various sauces. It was acid stable (pH3).

In the foregoing Examples, the norbixin could not be removed from the substrate by centrifugation at a neutral to acidic pH.

EXAMPLE 2

Demonstration of unique hue obtained with adduct, and increased tinctorial strength a. Coloration of milk. A 6.6& solution of pure potassium norbixin (so-called "cheese color") was diluted to 1.1% with water, and the dilute solution added with agitation to whole milk to give a level of 100 ppm norbixin in the milk. The resulting color was light orange.

Skim milk norbixin adduct powder made in Example 1(a) was diluted 1:10 with water, and added to the whole milk to a concentration of 50 ppm norbixin. The milk was raspberry in color, and of comparable intensity of color. At 100 ppm, it is expectedly stronger.

A possible explanation of the redder hue and greater tinctorial power of the adduct follows: Since the pH of the milk is below 7, the norbixin precipitates from the cheese color, dissolves in the butterfat, and the color is orange; in the product colored with the adduct, the norbixin remains as an adduct, which in color is raspberry and stronger at an equal level. This demonstrates the unique and unexpected properties of the adduct.

EXAMPLE 2b b. To demonstrate the difference in kind, and resulting difference in tinctorial power of the adduct as compared with free norbixin, the following substrates were prepared at a dilution of 1:100 in distilled water:
gelatin, 200 bloom (warmed to 35° C.)
gum arabic
polysorbate 80 (an oleaginous emulsifier used to make "acid proof" annatto colors).

The pH of each solution was raised to 10, one (1) ml of 6.6% norbixinate solution added, and the solutions were acidified over 5 minutes with 0.5% H3PO4, to form the adducts in the case of the gelatin and gum arabic, and emulsified norbixin in the case of polysorbate 80. These solutions were in turn diluted 1:100 in distilled water, with the pH thereof adjusted to 3. Spectra of the solutions were run, and the visual appearance noted.

In addition, 100 ml of soy bean oil, 50 ml of water, 1 ml of 6.6% norbixinate, and sufficient acid to reduce the pH to 5 were warmed to 50° C. and agitated for two hours to form a saturated solution of norbixin in soy oil. The oil was separated, filtered, and the spectrum run against soy oil as a blank, to show the spectrum of norbixin in soy oil.

The arabic adduct was clear red, the polysorbate 80 solution clear light orange. The adduct not only has about 10 times the absorbance of the polysorbate emulsified norbixin at 550 nm, but also only about 65% as much absorbance in the blue 460 nm region, which accounts for its red color as compared with the orange color of the norbixin dissolved in polysorbate 80.

Figure 2:
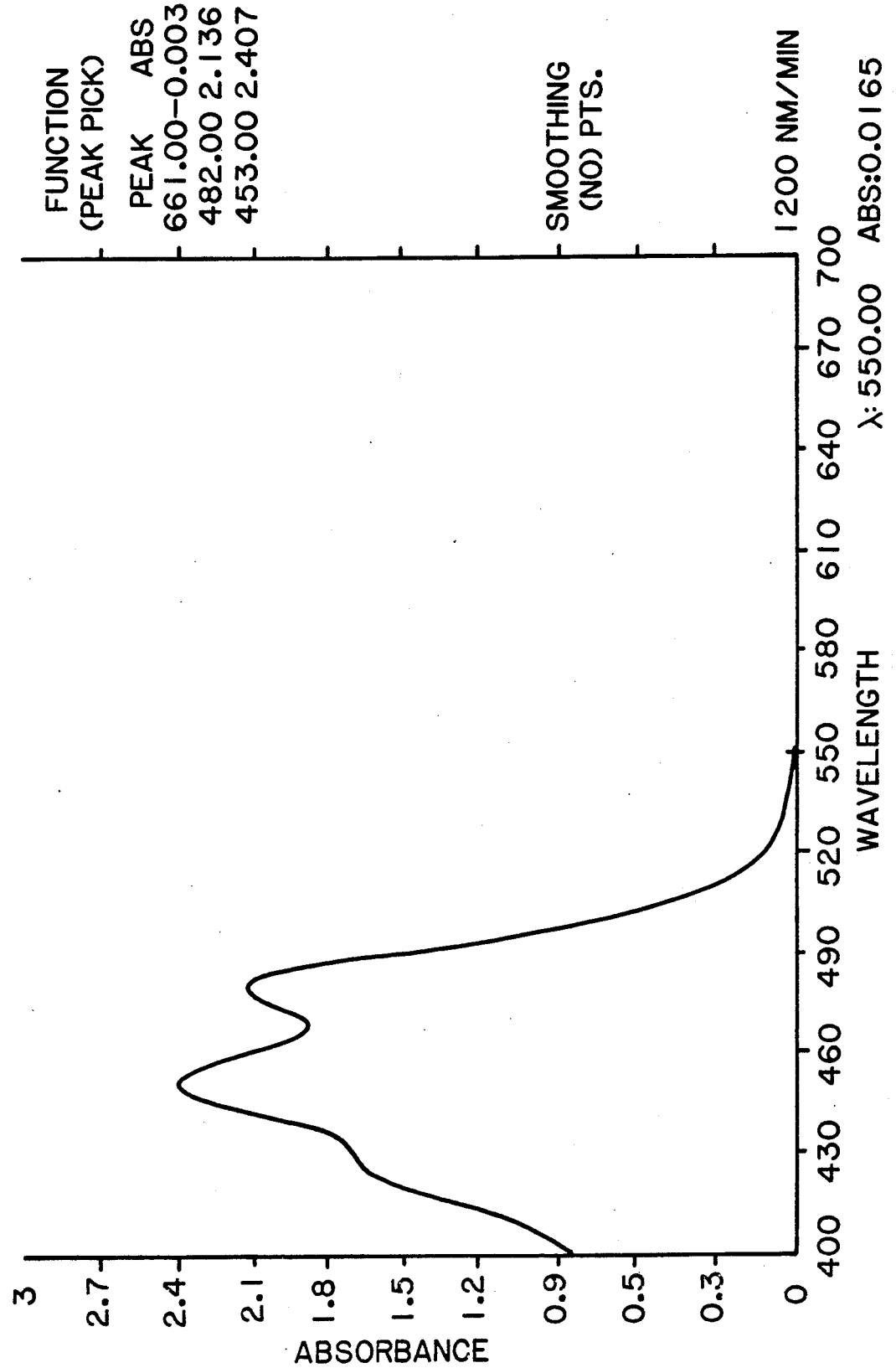
FIG. 2 is an absorption spectrum of norbixin plus polysorbate 80 diluted in water at pH3 and showing the characteristic peaks.
Figure 3:
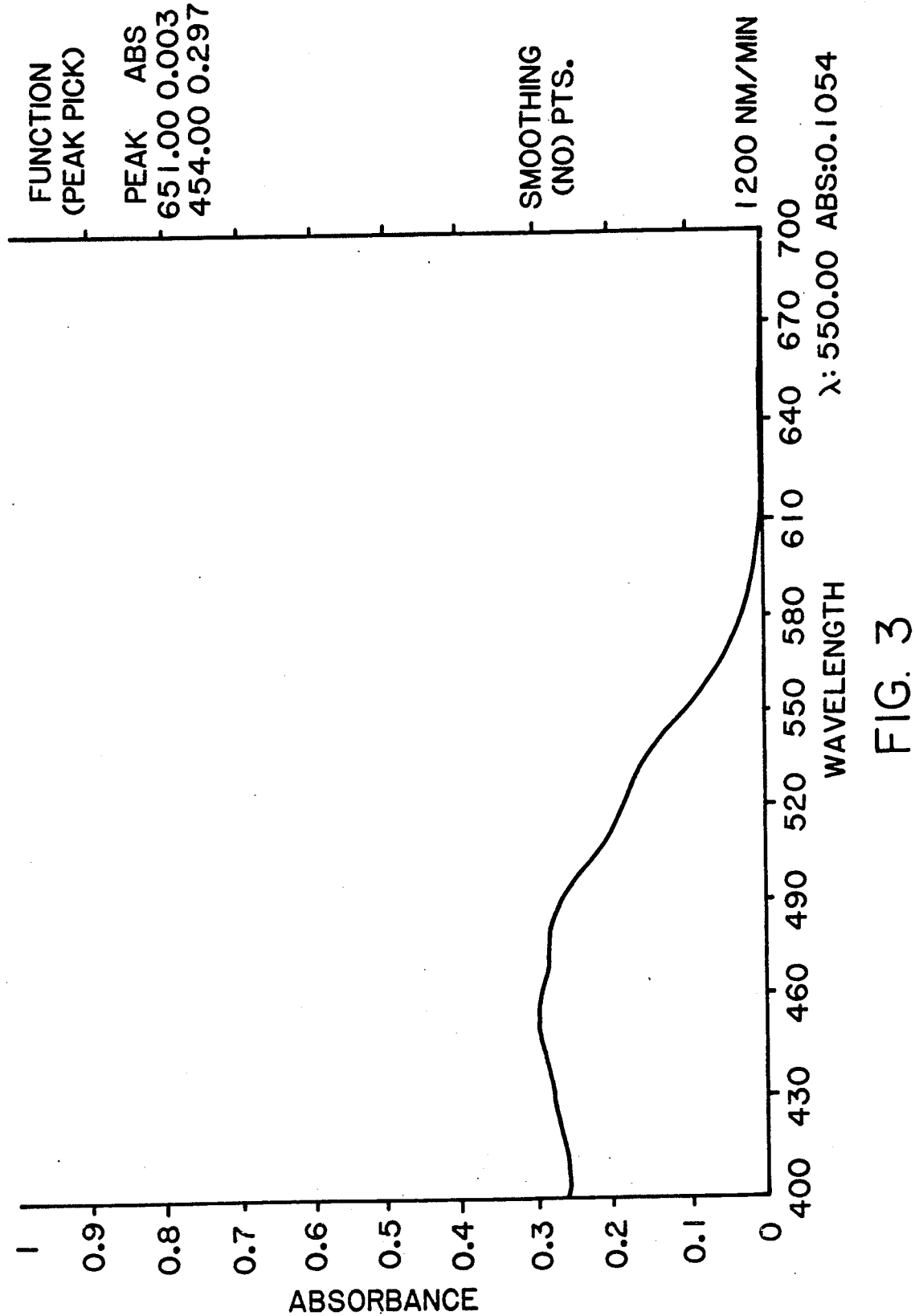
FIG. 3 is an absorption spectrum of a norbixin-gelatin adduct of the invention diluted in water at pH3 and again showing no peaks, but again showing considerable absorbance at 550 nm.
Figure 4:
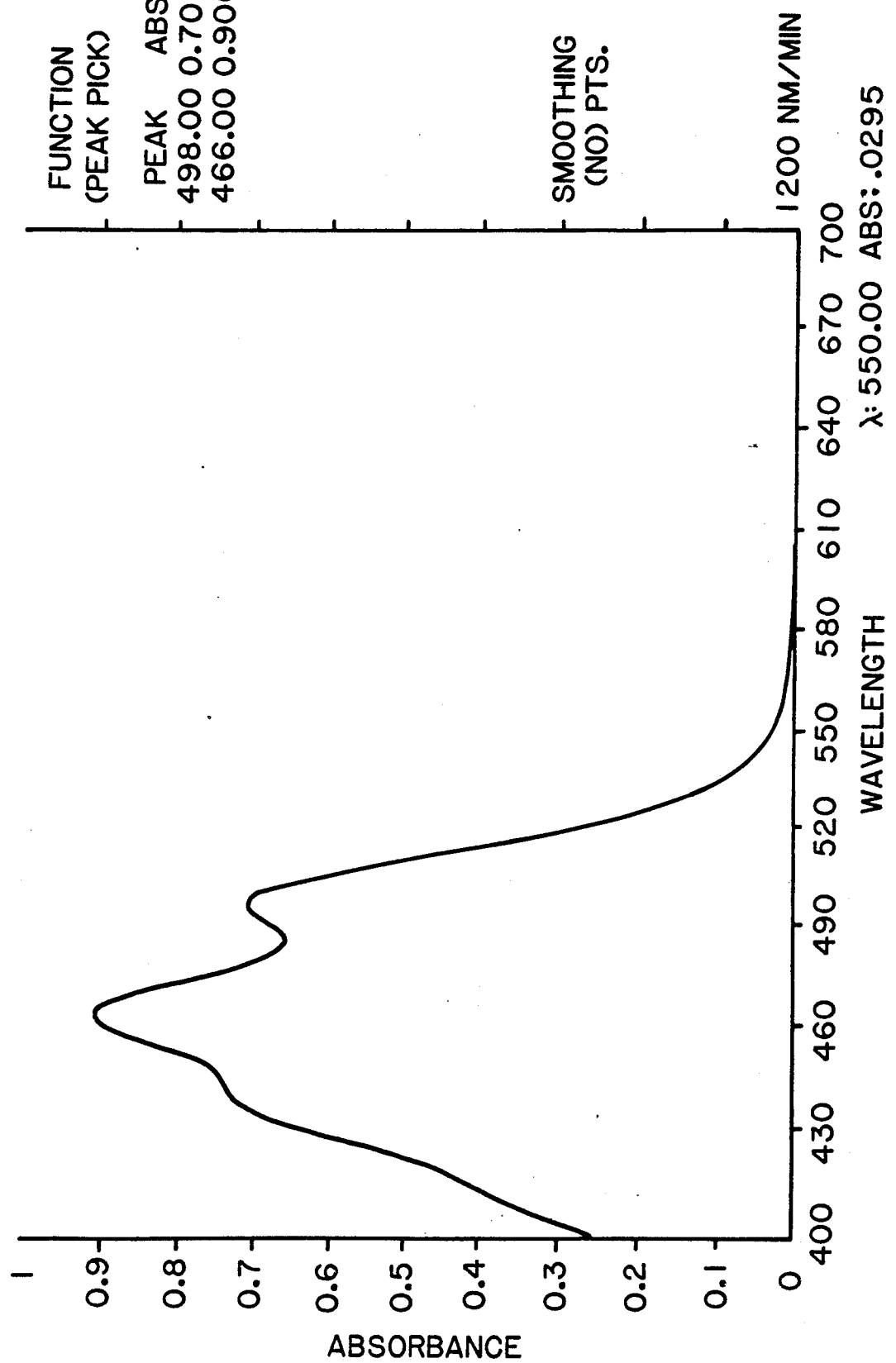
FIG. 4 is an absorption spectrum of norbixinate diluted in distilled water and again showing the characteristic peaks.
Figure 5:
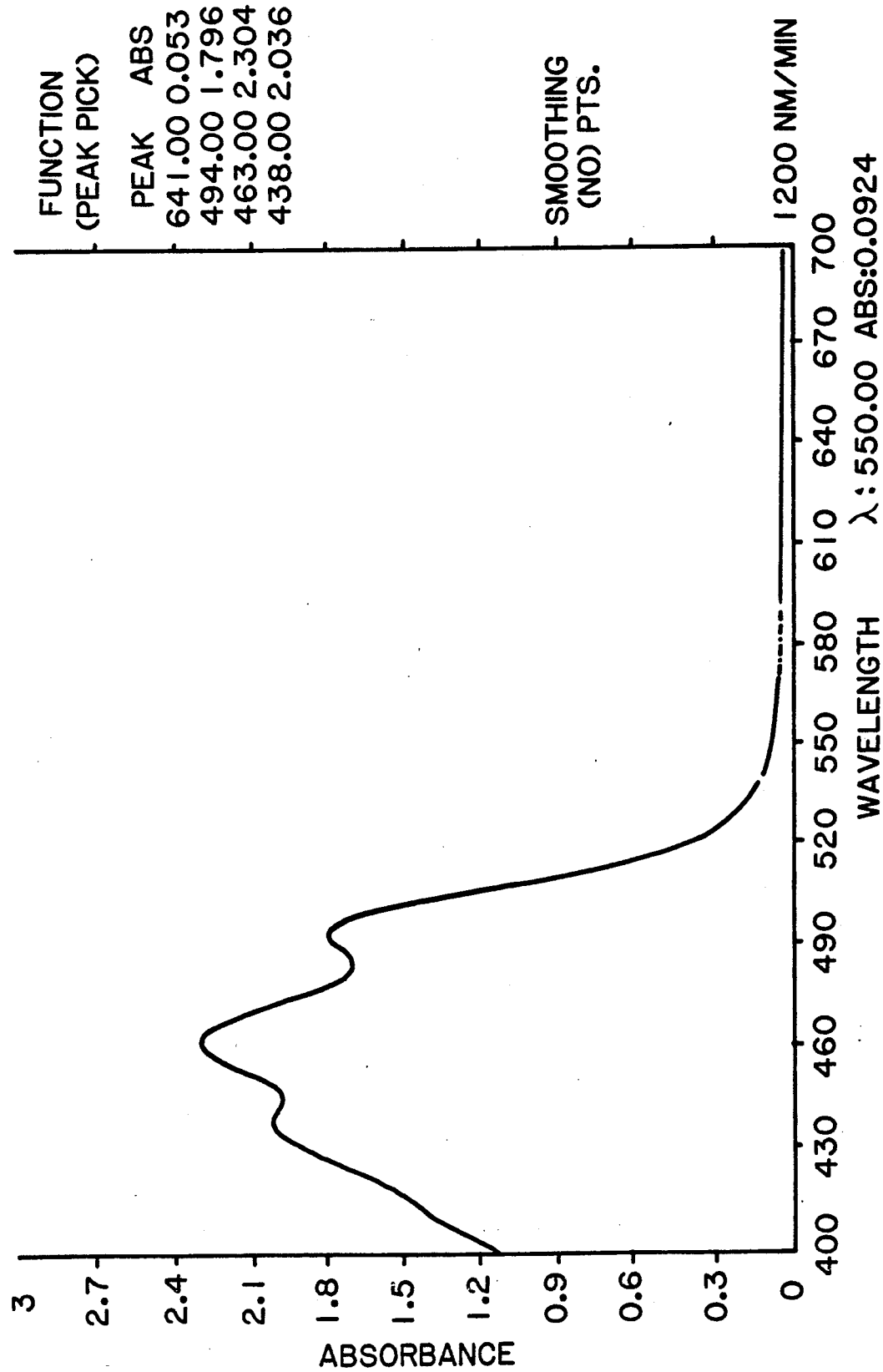
FIG. 5 is an absorption spectrum of soybean oil saturated with norbixin and diluted 50% in soybean oil, once again showing the characteristic peaks in the 430–490 nm range.

The spectra are shown in FIGS. 1-5. It is evident that they fall into two classes: spectra of free norbixin with two peaks in the 450-500 nm region, similar to the spectrum of norbixinate diluted in distilled water; and spectra of the adduct, having smooth curves and substantial absorbance at 550 nm in relation to the absorbance at 460 nm. This reflects the visual differences: the free norbixin in distilled water, polysorbate 80, and soy oil is orange, and the adduct is red-magenta.

The dilute solutions were allowed to stand on a table top under fluorescent light for one day. The polysorbate 80 solution became colorless, whereas the adducts retained their color. This demonstrates the greatly-enhanced light stability of the adduct as compared with free norbixin, which may be due to the change in the nature of the chromophore.

The adducts of the other water-soluble and water-dispersible proteins and branched-chain and cyclic polysaccharides mentioned in this specification behave the same way although, if the substrate is hazy, as in the case of skim milk, the dispersion of the adduct will also be hazy.

This again demonstrates the difference in kind between the product of the present invention and the norbixin of the prior art. The visual shade difference shown in part (a) of this Example is supported by this explanation and the technical evidence.

Therefore, the behavior of the adduct supports the inference to be drawn from the spectral characteristics: the adduct is a different chromophore than norbixin, or even norbixinate, per se. It should also be noted that the spectral curves of the adducts do not possess the typical double peaks in the 460 nm region (at ca. 490 and 466) which are characteristic of norbixin, besides having entirely different absorbancies at 460 and 550 nm, as noted above.

EXAMPLE 3

Use of various acids and base

Except for the lower solubility of sodium as compared to potassium norbixinate, the two ions are interchangeable. In place of phosphoric acid, sulfuric or hydrochloric may be substituted directly as in Example 2(b).

However, these acids are much more corrosive, and not readily handled in food plants. Organic acids, such as citric and lactic, may also be used and, because they are normal constituents of many foods, are advantageous in certain applications. However, phosphoric is the much preferred acid.

EXAMPLE 4

Criticality of relatively slow neutralization

Ionic reactions are instantaneous and, ordinarily, it would not appear necessary to slowly neutralize the solution of norbixinate and substrate. However, it appears to take a short time for the adduct to form during the neutralization process, and it is therefore preferred to drop the pH slowly over a period of a few minutes. If done in less than a minute, and especially less than 30 seconds, most of the norbixin appears to be precipitated in its free form, and the hue will be relatively orange and the tinctorial power relatively low.

A 1% solution of 40 bloom gelatin was prepared and the pH raised to 10. Then 1 ml of a 6.6% norbixinate solution was added, and the mixture allowed to stir for ten minutes at 25° C. A portion was neutralized to a pH of 6.5 in 30 seconds, a second portion in 1 minute, a third portion in 2 minutes, a fourth portion over 5 minutes, and a fifth portion over 10 minutes. A comparison of the hues and tinctorial strengths, following dilution of the solutions 1 to 20 with water, was as follows:

TABLE I

| Time | Hue | Strength |
| --- | --- | --- |
| 30 sec. | orange | weakest |
| 1 min. | red orange | intermediate |
| 5 min. | red | strongest |
| 10 min. | red | strongest |

This shows that less than thirty seconds is unsatisfactory, and that five minutes or more is preferred in practice.

EXAMPLE 5

Criticality of pH

There are two critical pH limitations to the process of forming the norbixin adduct.

a. The lower limit of the starting alkaline norbixinate solution is that pH at which substantially all of the dicarboxylic acid is in its salt form, and therefore soluble in the aqueous solution or suspension of substrate. If it is present as free norbixin, rather than norbixinate, the adduct will not form. This lower limit of the norbixinate solution can be determined by making a dilute solution of potassium norbixinate (200 ppm) and slowly acidifying it. At a pH of 8.5, it becomes hazy due to free norbixin being formed, and this is the lower limit of the pH for the norbixinate solution. Solubility will be limited in more concentrated norbixinate solutions at this pH, and the preferred lower pH limit is therefore at least about 9 and more preferably 10 to 12.

b. The upper limit of pH of the norbixin adduct solution is determined by the pH at which substantially all of the norbixinate has been converted to norbixin adduct. This pH is about 7.7, which can be determined by preparing a 2000 ppm gum arabic solution, filtering, adjusting pH to 10, and adding 200 ppm norbixinate.

The pH is then lowered stepwise, withdrawing samples for spectral analysis. The samples are diluted 1/100 in pH 3 water (pH 3 being chosen to show the remarkable stability of the adduct at this pH; a higher pH gives the same result), and the absorbance at 460 in the blue region and in the green (550 nm) recorded. In Table II, these absorbances are related to that of a sample taken at pH 6.7 as 100. No correction is made for dilution due to acidification, which would decrease the numbers below 100 slightly. It should be mentioned that the spectral curves of the adduct solutions are like that of the arabic adduct of Example 2(b), whereas the curves of the alkaline norbixinate solutions are similar to that of the polysorbate 80 solution of Example 2(b).

Table II shows that the absorbance in the green region of the spectrum (550 nm) due to the formation of the adduct is essentially complete at pH 7.7, but does increase further as the pH is lowered. It also shows that the absorbance in the blue region of the spectrum (460 nm) relative to that in the green region changes at pH 7.7 from that at 9, and increases somewhat more on further reduction of the pH, which demonstrates that the absorbtion spectrum of the adduct is very different from that of norbixinate and that of the free norbixin dissolved and emulsified in polysorbate 80 of Example 2(b).

TABLE II

| pH/nm | 550/460 | 550 |
| --- | --- | --- |
| 9.0 | 2.6 | 5.5 |
| 7.7 | 88 | 85 |
| 7.6 | 88 | 87 |
| 7.4 | 92 | 90 |
| 6.8 | 96 | 95 |
| 6.4 | 100 | 100 |

EXAMPLE 6

Comparative Example With Respect to Prior Art

The prior art (Schmidt U.S. Pat. No. 4,542,822) describes a powdered mixture of potassium norbixinate and Capsul TM, a modified amylopectin (branched-chain) starch. It is shown and claimed by Schmidt that the dry powdered form of potassium norbixinate and Capsul has unique properties of solubility in water at a pH of 3. The inventor shows that other branched-chain polysaccharides, namely gum arabic (a preferred form of this invention) and maltodextrins, are unsatisfactory.

The prior art preferred process was repeated except that ½ the amount (½ part) of 6.6% norbixinate solution per part Capsul was used, instead of one part of 3% of norbixinate strength cheese color, and the amount of water was doubled to 2 parts water to one part Capsul to reduce the viscosity of the Capsul solution and permit improved mixing. (When solutions are too viscous, neutralization is not evenly achieved without agitation so vigorous that air is whipped into the solution, which is disadvantageous.) Upon drying, this gives the pH 3 stable norbixinate powder of the prior art claims. In addition, the norbixinate-Capsul solution was slowly acidified to pH 6.5 to form the Capsul-norbixin adduct. In addition, a gum arabic solution was prepared, using the same proportions as above, a portion of which was acidified to form the adduct and a portion of which was left alkaline.

Upon addition to pH 3 buffered water, the adducts were red and stable; the non-adducted, non-acidified preparations were weak orange, and the gum arabic preparation precipitated. The Capsul-norbixinate (non-adduct) precipitated after one day, whereas both adducts continued to color the solutions red. None of the gum arabic adduct, and only a portion of the Capsul adduct, precipitated. The arabic solution was particularly clear and therefore superior.

This vividly demonstrates both the solubility and tinctorial differences between the adduct and the non-adduct norbixinate preparations, particularly when tested by the methods of the art, as shown in Schmidt. Further, the appearance in acidic water of the non-adduct Capsul product was similar to that of the polysorbate 80 product of Example 2(b), whereas the Capsul-norbixin adduct had the characteristics of the arabic adduct.

If the proportions of norbixinate to Capsul and arabic are doubled, the Capsul adduct becomes duller in color and tends to precipitate, whereas the arabic adduct remains red and soluble. This points out a difference between the preferred adduct substrate, arabic, and modified starch. However, because the latter is cheaper, it may be the most economical substrate for many applications. One skilled in the art can tailor the substrate to the desired use in food. (For the non-adduct norbixinate of Schmidt, Capsul is indeed superior to arabic.)

EXAMPLE 7

Criticality of branched-chain polysaccharide

Microcrystalline cellulose and guar gum are two examples of straight-chain polysaccharides widely used to impart viscosity to foods. These do not form adducts with norbixin as shown by their coloration and behavior.

Microcrystalline cellulose (Avicel TM) (10 g), 180 ml of water, and 15 ml of 6.6% norbixinate solution, which turned the solution alkaline, were brought to a boil and 2.5 g of NaCl added. The mixture was agitated for ten minutes but, being a thick paste, it would not filter. By admixing with ½ volume of diatomaceous earth, it could be filtered. The resulting powder, washed with water and then dilute acetic acid, was brownish.

Because of the difficulties with filtration, the experiment was repeated using cellulose fiber (Kleenex TM) which was disintegrated in a blender. The resulting pulp was dewatered by pressing, and again the resulting dry product was brownish with a reddish cast.

Guar gum was hydrated in water (2 g/400 ml) overnight, resulting in a viscous solution. (More concentrated solutions would not stir.) Then 2 ml of a 6.6% norbixinate solution, of 8% KOH concentration, was added. The resulting pH was 10.7.

This solution was evaluated in four ways:
1. Boiling, with the addition of 2.5% NaCl.
   a. not acidified
   b. acidified to pH 6.5 slowly (15 minutes)
2. 30° C., without salt.
   a. not acidified
   b. acidified to pH 6.5 slowly (17 minutes)

These solutions were in turn diluted 1:20 in distilled water and observed.

The observations were as follows:

1(a) and 2(a) were orange, same color as norbixinate, above precipitated cellulose fiber, due to alkalinity and dissolution of norbixinate in water.

1(b) was orange, similar to norbixinate in color, hazy.

2(b) was brownish-red, hazy, threw precipitate separate from gum.

Furthermore, products 1(a) and 1(b) were dried and powdered. The powder of 1(a) was orange brown, and that of 1(b) reddish brown.

This demonstrates that the prior art use of salt as a fixing agent, even with slow acidification (prior art uses instantaneous neutralization), does not produce the red adduct, although a fixing agent such as salt is believed by the prior art to be beneficial. (The present invention and application does not find a fixing agent to be useful.) Because of insoluble material, spectra could not be run.

EXAMPLE 8

Cyclodextrins and other substrates

Although water-soluble and water-dispersible branched-chain polysaccharides and water-soluble and water-dispersible proteins are encompassed by the concept of this invention, and representative items such as high ethoxy pectin, propylene glycol alginate, gums guar and karaya, carrageenan, and maltodextrins made from amylopectins (a branched-chain starch), as well as so-called "modified starches" in general, and casein, hydrolyzed soy protein, and high protein flours such as mustard, are also suitable substrates for forming an adduct of the invention, a unique adduct can be formed with a conical, cyclic saccharide called a cyclodextrin.

For example, 4 g of beta cyclodextrin was dissolved in hot water (50° C.), and the pH adjusted to 10. Then 2 ml of a 6.6% norbixinate solution was added, and the mixture neutralized over 10 minutes at 40° C. to pH 6 with phosphoric acid. The resulting deep orange red solution was clear. Upon cooling, the adduct precipitated due to insolubility of cyclodextrin. The precipitate, when redissolved in water, gave a clear orange-red solution at pH 3.

EXAMPLE 9

Mixtures of adduct with water-soluble edible solvents

The gum arabic-norbixin adduct of Example 1(c) was mixed with propylene glycol to give solutions containing 25% and 50% propylene glycol. Both solutions were stable and gave bright red colors when added to water.

Likewise, a solution containing 25% ethanol was prepared, with the same results.

Other solvents, such as glycerine, ethanol, and isopropanol, which are conventionally used in foods, are suitable diluents and bacteriostatic agents. The use of such solvents permits preparation of stable liquid forms of this invention, which are not subject to bacteriological attack.

The presence of such solvents during the process of the invention does not interfere with complexing of the norbixin, as already stated, and in some cases is a preferred aspect of the process of the invention, as when a liquid form of the norbixin complex or adduct is to be used directly in a food or beverage.

Of course, the water solutions themselves can be used directly by adding to the food if they are protected from spoilage.

EXAMPLE 10

Preparation of coacervates

The term "coacervate" is here used in accordance with its common understanding to mean an aggregate of colloidal droplets held together by electrostatic attraction.

An adduct employing a coacervate of gelatin and gum arabic was made as follows: 6 g of 200 bloom gelatin was dissolved in 200 ml of 40° C. water. Then 6 g of gum arabic was similarly dissolved. The solutions were mixed, and immediately became cloudy as the coacervate formed. The pH was raised to 10 at which point the solution clarified. Then 6 ml of 6.6% norbixinate were added and the mixture agitated 10 minutes and then slowly acidified to pH 6.5 to form the adduct and reform the coacervate. Upon addition of the coacervate-adduct to water, it gave a bright red, clear solution, superior in chroma and redder than equivalent concentrations of either the gelatin or gum arabic adduct alone.

It should be understood that coacervates may be made in the same manner but using substrates other than the above, and by increasing ion levels in the aqueous media, which procedures are also contemplated by this specification.

EXAMPLE 11

Applications of adduct in the coloring of foods

The adduct of the invention, in powdered or liquid form, may be added directly to foods. For example, the spray-dried skim milk powder, added to yogurt, gives it a strawberry hue. When added to a milkshake, it will give it an orange to red hue, depending upon the level of addition.

The gum arabic or other polysaccharide adduct may be added to a juice, such as a vegetable juice, to enhance its brightness and redness. It may be combined with a complex of curcumin with a similar substrate to give a yellow-orange color. It may be added to orange juice to provide a deeper hue, or to an orange drink, in combination with complexed curcumin, to soften the yellow of curcumin.

Its use in imparting color to glazes is obvious, as well as in cheese sauces and barbecue flavors. Dusted on snacks, bright red colors can be achieved. The protein adducts, in particular, are useful for coloration of meats and gravies.

Many other applications will be apparent to the food technologist. The color is natural in origin, and offers a convenient replacement for the objectionable so-called "coal-tar" colors for the coloration of foods.

It is thus seen that the present invention provides a novel, water-soluble, clear, and adaptable norbixin which provides a reddish to magenta color, which differs in kind from the prior art product which provides an orange color, being a complex or adduct of norbixin formed on a substrate in alkaline solution, and then neutralized and acidified to its acidic form as a complex on the substrate. This novel complex is shown to have unique properties not available to the prior art.

Critical to the present invention is the dissolution of norbixin in alkaline solution, admixing with a substrate which may be a water-soluble or water-dispersible branched-chain or cyclic polysaccharide or a water-soluble or water-dispersible protein, and acidification. The substrate may be a common component of food, which has value in itself, and which is compatible with food in which the color is used. Coloring to taste is readily achieved.

A remarkable, valuable, and surprising discovery is the novel and improved tinctorial power and stability of the complex or adduct of the present invention when compared with prior art norbixin products.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

I claim:

1. A process for preparing a red to magenta complex of norbixin and a substrate selected from the group consisting of a water-soluble branched-chain polysaccharide, a water-dispersible branched-chain polysaccharide, a cyclic polysaccharide, a water-soluble protein and a water-dispersible protein, which consists essentially of admixing the substrate and norbixin in an aqueous solution at a pH above about 8.5, at which pH the norbixin is present in its water-soluble orange alkaline form, and then acidifying to drop the pH to below about 7.7, thereby complexing the norbixin in the reddish or magenta form of its complex.

2. A process of claim 1, wherein the substrate is selected from the group consisting of milk protein, sodium caseinate, whey, gelatin, modified food starch, pectin, a vegetable gum, propylene glycol alginate, cyclodextrin, maltodextrin derived from amylopectin, and carboxymethylcellulose.

3. A process of claim 1, wherein the pH of the aqueous solution prior to acidification is above about 9 and the pH after acidification is below about 6.8.

4. A process of claim 3 wherein the pH of the aqueous solution is about 9-12 and the pH after acidification is about 6-6.7.

5. A process of claim 2, wherein the norbixin complex is formed into a coascervate.

6. A process of claim 2, wherein the norbixin is complexed with a combination of substrates.

7. A process of claim 6 wherein the combination of norbixin complexes is formed into a coascervate.

8. A process of claim 2, wherein the substrate is a combination of gelatin and a vegetable gum.

9. A process of claim 8, wherein the combination of norbixin complexes is formed into a coascervate.

10. A process of claim 2, wherein the substrate is a combination of gelatin and gum arabic.

11. A process of claim 10, wherein the combination of norbixin complexes is formed into a coascervate.

12. A process of claim 2, wherein the substrate is gelatin, gum arabic, gum karaya, gum ghatti, modified food starch, cyclodextrin, or carboxymethylcellulose.

13. A process of claim 1, wherein the substrate is cyclodextrin.

14. A process of claim 1, wherein the process is carried out in the presence of a water-miscible, non-acidic solvent which does not interfere with the complexing of the alkaline norbixin with the substrate.

15. A process of claim 14, wherein the solvent is selected from the group consisting of alcohols, glycerine, and propylene glycol.

16. A process of claim 14, wherein the solvent is ethyl alcohol, isopropyl alcohol, glycerine, or propylene glycol.

17. A red to magenta norbixin complex consisting essentially of norbixin complexed with a substrate selected from the group consisting of a water-soluble branched-chain polysaccharide of a water-dispersible branched-chain polysaccharide, a cyclic polysaccharide, a water-soluble protein and a water-dispersible protein, which will not precipitate upon standing in water which gives an essentially stable reddish or magenta solution in water at a pH of 3 to 4, which has an increased absorption at 550 nm and a reduced absorption in the 460-550 nm range when compared with norbixin or norbixinate, and from which norbixin complex the norbixin per se cannot be removed by centrifugation at a neutral to acidic pH.

18. A complex of claim 17, wherein the substrate is selected from the group consisting of milk protein, sodium caseinate, whey, gelatin, modified food starch, pectin, a vegetable gum, propylene glycol alginate, cyclodextrin, maltodextrin derived from amylopectin, and carboxymethylcellulose.

19. A red to magenta norbixin complex consisting essentially of norbixin complexed with a substrate selected from the group consisting of a water-soluble branched-chain polysaccharide, a water-dispersible branched-chain polysaccharide, a cyclic polysaccharide, a water-soluble protein and a water-dispersible protein, the norbixin being complexed to the substrate by slow acidification from an alkaline solution of norbixin and substrate.

20. A red to magenta norbixin complex consisting essentially of norbixin complexed with a substrate selected from the group consisting of a water-soluble branched-chain polysaccharide, a water-dispersible branched-chain polysaccharide, a cyclic polysaccharide, a water-soluble protein and a water-dispersible protein, by a process which consists essentially of contacting the substrate and norbixin in an aqueous solution at a pH above about 8.5, at which pH the norbixin is present in its water-soluble orange alkaline form, and then acidifying to drop the pH to below about 7.7, thereby complexing the norbixin in the reddish form of its complex with the substrate.

21. A red to magenta norbixin complex consisting essentially of norbixin complexed with a substrate selected from the group consisting of a water-soluble branched-chain polysaccharide, a water-dispersible branched-chain polysaccharide, a cyclic polysaccharide, a water-soluble protein and a water-dispersible protein, according to the procedure of claim 2.

22. A red to magenta norbixin complex consisting essentially of norbixin complexed with a substrate selected from the group consisting of a water-soluble branched-chain polysaccharide, a water-dispersible branched-chain polysaccharide, a cyclic polysaccharide, a water-soluble protein and a water-dispersible protein, according to the procedure of claim 3.

23. A red to magenta norbixin complex produced according to the procedure of claim 4.

24. A red to magenta norbixin complex produced according to the procedure of claim 5.

25. A red to magenta norbixin complex produced according to the procedure of claim 6.

26. A red to magenta norbixin complex produced according to the procedure of claim 7.

27. A red to magenta norbixin complex produced according to the procedure of claim 8.

28. A red to magenta norbixin complex produced according to procedure of claim 9.

29. A red to magenta norbixin complex produced according to the procedure of claim 10.

30. A red to magenta norbixin complex produced according to the procedure of claim 11.

31. A red to magenta norbixin complex produced according to the procedure of claim 12.

32. A red to magenta norbixin complex produced according to the procedure of claim 13.

33. A red to magenta norbixin complex produced according to the procedure of claim 14.

34. A red to magenta norbixin complex produced according to the procedure of claim 15.

35. The process consisting essentially of mixing norbixin and liquid whey or skim milk, agitating the mixture at an alkaline pH above about 8.5, dropping the pH to below about 7.7 thereby producing a red to magenta color, and then drying.

36. A dry milk solid product produced by the method of claim 35.

37. A food or beverage colored with a red to magenta adduct of norbixin with a water-soluble or water-dispersible protein or branched-chain or cyclic polysaccharide.

38. A food product of claim 37 wherein the adduct is in dried and powdered form.

39. A food product of claim 37 wherein the adduct is in liquid form.

40. The process of claim 1 wherein the pH above about pH 8.5 is effected with NaOH or KOH.

41. The process of claim 40 wherein the downward pH adjustment is effected using phosphoric acid.

* * * * *

UNITED STATES PATENT AND TRADEMARK OFFICE
CERTIFICATE OF CORRECTION

PATENT NO. : 5,053,240

DATED : Oct. 1, 1991

INVENTOR(S) : Paul H. Todd, Jr.

It is certified that error appears in the above-identified patent and that said Letters Patent is hereby corrected as shown below:

Column 14, line 39; change "of" to a comma.

Column 14, line 43; "water which" should read -- water, which --.

Column 15, line 8; "reddish form" should read -- reddish to magenta form --.

Signed and Sealed this

First Day of June, 1993

Attest:

MICHAEL K. KIRK

*Attesting Officer*    Acting Commissioner of Patents and Trademarks